(12) United States Patent
Casey (10) Patent No.: US 8,016,874 B2
(45) Date of Patent: Sep. 13, 2011

(54) FLEXIBLE STENT WITH ELEVATED SCAFFOLDING PROPERTIES

(75) Inventor: Brendan J. Casey, Galway (IE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 82 days.

(21) Appl. No.: 11/805,584

(22) Filed: May 23, 2007

(65) Prior Publication Data

US 2008/0294239 A1   Nov. 27, 2008

(51) Int. Cl.
*A61F 2/06* (2006.01)
(52) U.S. Cl. .............................. 623/1.15; 623/1.16
(58) Field of Classification Search .................. None
See application file for complete search history.

(56) References Cited

U.S. PATENT DOCUMENTS

| | | |
|---|---|---|
| 4,475,972 A | 10/1984 | Wong |
| 4,580,568 A | 4/1986 | Gianturco |
| 4,738,740 A | 4/1988 | Pinchuk et al. |
| 4,743,252 A | 5/1988 | Martin, Jr. et al. |
| 4,759,757 A | 7/1988 | Pinchuk |
| 4,776,337 A | 10/1988 | Palmaz |
| 4,800,882 A | 1/1989 | Gianturco |
| 4,907,336 A | 3/1990 | Gianturco |
| 5,015,253 A | 5/1991 | MacGregor |
| 5,041,126 A | 8/1991 | Gianturco |
| 5,059,211 A | 10/1991 | Stack et al. |
| 5,102,417 A | 4/1992 | Palmaz |
| 5,104,404 A | 4/1992 | Wolff |
| 5,116,360 A | 5/1992 | Pinchuk et al. |
| 5,122,154 A | 6/1992 | Rhodes |
| 5,133,732 A | 7/1992 | Wiktor |
| 5,147,370 A | 9/1992 | McNamara et al. |
| 5,163,951 A | 11/1992 | Pinchuk et al. |
| 5,171,262 A | 12/1992 | MacGregor |
| 5,221,261 A | 6/1993 | Termin et al. |
| 5,282,823 A | 2/1994 | Schwartz et al. |
| 5,292,331 A | 3/1994 | Boneau |
| 5,314,444 A | 5/1994 | Gianturco |

(Continued)

FOREIGN PATENT DOCUMENTS

CA    2309079    11/2004

(Continued)

OTHER PUBLICATIONS

U.S. Appl. No. 11/973,707, mailed Jun. 9, 2009, Office Action.

(Continued)

*Primary Examiner* — David Isabella
*Assistant Examiner* — Seema Swaminathan
(74) *Attorney, Agent, or Firm* — Workman Nydegger (57) ABSTRACT

A stent is disclosed that generates an elevated degree of scaffolding to a bodily vessel while retaining a highly flexible structure. In one embodiment, a stent includes an essentially tubular body formed by a web structure that is configured to expand from a contracted delivery configuration to an expanded deployed configuration and that is composed of a plurality of longitudinally adjacent web rings. Those web rings are formed by a plurality of web elements disposed circumferentially around the longitudinal axis of the stent and adjoined one to the other with a junction bend. Each junction bend in a first web ring is coupled to another junction bend in a neighboring ring with as-shaped connector, and the coupled junction bends are not longitudinally aligned but are instead laterally offset.

23 Claims, 6 Drawing Sheets

U.S. PATENT DOCUMENTS

| | | |
|---|---|---|
| 5,370,683 A | 12/1994 | Fontaine |
| 5,378,239 A | 1/1995 | Termin et al. |
| 5,380,299 A | 1/1995 | Fearnot et al. |
| 5,421,955 A | 6/1995 | Lau et al. |
| 5,443,458 A | 8/1995 | Eury |
| 5,443,496 A | 8/1995 | Schwartz et al. |
| 5,449,373 A | 9/1995 | Pinchasik et al. |
| 5,476,508 A | 12/1995 | Amstrup |
| 5,496,277 A | 3/1996 | Termin et al. |
| 5,514,154 A | 5/1996 | Lau et al. |
| 5,527,354 A | 6/1996 | Fontaine et al. |
| 5,556,414 A | 9/1996 | Turi |
| 5,569,295 A | 10/1996 | Lam |
| 5,591,197 A | 1/1997 | Orth et al. |
| 5,591,224 A | 1/1997 | Schwartz et al. |
| 5,593,417 A | 1/1997 | Rhodes |
| 5,593,442 A | 1/1997 | Klein |
| 5,603,721 A | 2/1997 | Lau et al. |
| 5,609,606 A | 3/1997 | O'Boyle |
| 5,628,788 A | 5/1997 | Pinchuk |
| 5,630,829 A | 5/1997 | Lauterjung |
| 5,632,772 A | 5/1997 | Alcime et al. |
| 5,639,278 A | 6/1997 | Dereume et al. |
| 5,649,952 A | 7/1997 | Lam |
| 5,651,174 A | 7/1997 | Schwartz et al. |
| 5,653,747 A | 8/1997 | Dereume |
| 5,670,161 A | 9/1997 | Healy et al. |
| 5,674,242 A | 10/1997 | Phan et al. |
| 5,674,277 A | 10/1997 | Freitag |
| 5,693,085 A | 12/1997 | Buirge et al. |
| 5,695,516 A | 12/1997 | Fischell et al. |
| 5,697,971 A | 12/1997 | Fischell et al. |
| 5,700,285 A | 12/1997 | Myers et al. |
| 5,707,386 A | 1/1998 | Schnepp-Pesch et al. |
| 5,707,388 A | 1/1998 | Lauterjung |
| 5,709,703 A | 1/1998 | Lukic et al. |
| 5,709,713 A | 1/1998 | Evans et al. |
| 5,716,393 A | 2/1998 | Lindenberg et al. |
| 5,723,003 A | 3/1998 | Winston et al. |
| 5,723,004 A | 3/1998 | Dereume et al. |
| 5,728,158 A | 3/1998 | Lau et al. |
| 5,733,303 A | 3/1998 | Israel et al. |
| 5,735,892 A | 4/1998 | Myers et al. |
| 5,735,893 A | 4/1998 | Lau et al. |
| 5,735,897 A | 4/1998 | Buirge |
| 5,738,817 A | 4/1998 | Danforth et al. |
| 5,741,325 A | 4/1998 | Chaikof et al. |
| 5,741,327 A | 4/1998 | Frantzen |
| 5,743,874 A | 4/1998 | Fischell et al. |
| 5,749,880 A | 5/1998 | Banas et al. |
| 5,755,771 A | 5/1998 | Penn et al. |
| 5,755,772 A | 5/1998 | Evans et al. |
| 5,755,774 A | 5/1998 | Pinchuk |
| 5,755,781 A | 5/1998 | Jayaraman |
| 5,769,884 A | 6/1998 | Solovay |
| 5,776,161 A | 7/1998 | Globerman |
| 5,776,181 A | 7/1998 | Lee et al. |
| 5,776,183 A | 7/1998 | Kanesaka et al. |
| 5,800,526 A | 9/1998 | Anderson et al. |
| 5,807,404 A | 9/1998 | Richter |
| 5,810,868 A | 9/1998 | Lashinski et al. |
| 5,810,870 A | 9/1998 | Myers et al. |
| 5,810,872 A | 9/1998 | Kanesaka et al. |
| 5,814,063 A | 9/1998 | Freitag |
| 5,817,126 A | 10/1998 | Imran |
| 5,824,037 A | 10/1998 | Fogarty et al. |
| 5,824,045 A | 10/1998 | Alt |
| 5,824,048 A | 10/1998 | Tuch |
| 5,824,054 A | 10/1998 | Khosravi et al. |
| 5,824,059 A | 10/1998 | Wijay |
| 5,827,321 A | 10/1998 | Roubin et al. |
| 5,836,964 A | 11/1998 | Richter |
| 5,836,966 A | 11/1998 | St. Germain |
| 5,843,120 A | 12/1998 | Israel et al. |
| 5,843,158 A | 12/1998 | Lenker et al. |
| 5,843,161 A | 12/1998 | Solovay |
| 5,843,164 A | 12/1998 | Frantzen et al. |
| 5,846,247 A | 12/1998 | Unsworth et al. |
| 5,853,419 A | 12/1998 | Imran |
| 5,855,598 A | 1/1999 | Pinchuk |
| 5,855,600 A | 1/1999 | Alt |
| 5,860,999 A | 1/1999 | Schnepp-Pesch et al. |
| 5,861,027 A | 1/1999 | Trapp |
| 5,868,781 A | 2/1999 | Killion |
| 5,871,538 A | 2/1999 | Dereume |
| 5,876,449 A | 3/1999 | Starck et al. |
| 5,876,450 A | 3/1999 | Johlin, Jr. |
| 5,895,406 A | 4/1999 | Gray et al. |
| 5,897,589 A | 4/1999 | Cottenceau et al. |
| 5,922,021 A | 7/1999 | Jang |
| 5,928,248 A | 7/1999 | Acker |
| 5,938,682 A | 8/1999 | Hojeibane et al. |
| 5,948,018 A | 9/1999 | Dereume et al. |
| 5,954,743 A | 9/1999 | Jang |
| 5,968,091 A | 10/1999 | Pinchuk et al. |
| 5,980,552 A | 11/1999 | Pinchasik et al. |
| 5,984,965 A | 11/1999 | Knapp et al. |
| 6,017,365 A | 1/2000 | Von Oepen |
| 6,019,789 A | 2/2000 | Dinh et al. |
| 6,027,526 A | 2/2000 | Limon et al. |
| 6,033,433 A | 3/2000 | Ehr et al. |
| 6,033,434 A | 3/2000 | Borghi |
| 6,033,435 A | 3/2000 | Penn et al. |
| 6,039,756 A | 3/2000 | Jang |
| 6,048,361 A | 4/2000 | Von Oepen |
| 6,059,811 A | 5/2000 | Pinchasik et al. |
| 6,068,656 A | 5/2000 | Von Oepen |
| 6,071,308 A | 6/2000 | Ballou et al. |
| 6,086,610 A | 7/2000 | Duerig et al. |
| 6,099,561 A | 8/2000 | Alt |
| 6,106,548 A | 8/2000 | Roubin et al. |
| 6,113,627 A | 9/2000 | Jang |
| 6,117,165 A | 9/2000 | Becker |
| 6,117,535 A | 9/2000 | Szycher et al. |
| 6,123,721 A | 9/2000 | Jang |
| 6,132,460 A | 10/2000 | Thompson |
| 6,165,212 A | 12/2000 | Dereume et al. |
| 6,174,326 B1 | 1/2001 | Kitaoka et al. |
| 6,179,868 B1 | 1/2001 | Burpee et al. |
| 6,190,403 B1 | 2/2001 | Fischell et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,335 B1 | 3/2001 | Igaki |
| 6,203,569 B1 | 3/2001 | Wijay |
| 6,231,598 B1 | 5/2001 | Berry et al. |
| 6,231,600 B1 | 5/2001 | Zhong |
| 6,241,762 B1 | 6/2001 | Shanley |
| 6,253,443 B1 | 7/2001 | Johnson |
| 6,258,116 B1 | 7/2001 | Hojeibane |
| 6,261,318 B1 | 7/2001 | Lee et al. |
| 6,264,688 B1 | 7/2001 | Herklotz et al. |
| 6,264,690 B1 | 7/2001 | Von Oepen |
| 6,270,524 B1 | 8/2001 | Kim |
| 6,273,913 B1 | 8/2001 | Wright et al. |
| 6,299,604 B1 | 10/2001 | Ragheb et al. |
| 6,299,635 B1 | 10/2001 | Frantzen |
| 6,325,825 B1 | 12/2001 | Kula et al. |
| 6,331,189 B1 | 12/2001 | Wolinsky et al. |
| 6,332,089 B1 | 12/2001 | Acker et al. |
| 6,340,366 B2 | 1/2002 | Wijay |
| 6,348,065 B1 | 2/2002 | Brown et al. |
| 6,377,835 B1 | 4/2002 | Schoenberg et al. |
| 6,395,020 B1 | 5/2002 | Ley et al. |
| 6,436,132 B1 | 8/2002 | Patel et al. |
| 6,451,049 B2 | 9/2002 | Vallana et al. |
| 6,485,508 B1 | 11/2002 | McGuinness |
| 6,488,702 B1 | 12/2002 | Besselink |
| 6,491,718 B1 | 12/2002 | Ahmad |
| 6,503,272 B2 * | 1/2003 | Duerig et al. ................ 623/1.24 |
| 6,506,211 B1 | 1/2003 | Skubitz et al. |
| 6,508,834 B1 | 1/2003 | Pinchasik et al. |
| 6,540,776 B2 | 4/2003 | Sanders Millare et al. |
| 6,558,415 B2 | 5/2003 | Thompson |
| 6,572,646 B1 | 6/2003 | Boylan et al. |
| 6,589,276 B2 | 7/2003 | Pinchasik et al. |
| 6,602,285 B1 | 8/2003 | Von Oepen et al. |

| | | |
|---|---|---|
| 6,607,554 B2 | 8/2003 | Dang et al. |
| 6,616,689 B1 | 9/2003 | Ainsworth et al. |
| 6,624,097 B2 | 9/2003 | Martin et al. |
| D481,139 S | 10/2003 | Seibold et al. |
| 6,629,994 B2 | 10/2003 | Gomez et al. |
| 6,679,911 B2 | 1/2004 | Burgermeister |
| 6,682,554 B2 | 1/2004 | Oepen et al. |
| 6,723,119 B2 | 4/2004 | Pinchasik et al. |
| 6,730,252 B1 | 5/2004 | Teoh et al. |
| 6,740,114 B2 | 5/2004 | Burgermeister |
| 6,749,629 B1 | 6/2004 | Hong et al. |
| 6,755,856 B2 | 6/2004 | Fierens et al. |
| 6,776,794 B1 | 8/2004 | Hong et al. |
| 6,786,922 B2 | 9/2004 | Schaeffer |
| 6,790,227 B2 | 9/2004 | Burgermeister |
| 6,796,999 B2 | 9/2004 | Pinchasik |
| 6,821,292 B2 | 11/2004 | Pazienza et al. |
| 6,846,323 B2 | 1/2005 | Yip et al. |
| 6,875,228 B2 | 4/2005 | Pinchasik et al. |
| 6,881,222 B2 | 4/2005 | White et al. |
| 6,913,619 B2 | 7/2005 | Brown et al. |
| 6,916,336 B2 * | 7/2005 | Patel et al. ............ 623/1.16 |
| 6,929,660 B1 | 8/2005 | Ainsworth et al. |
| 6,942,689 B2 | 9/2005 | Majercak |
| 6,955,686 B2 | 10/2005 | Majercak |
| 6,998,060 B2 | 2/2006 | Tomonto |
| 7,029,493 B2 | 4/2006 | Majercak et al. |
| 7,060,093 B2 | 6/2006 | Dang et al. |
| 7,128,756 B2 | 10/2006 | Lowe et al. |
| 7,141,062 B1 | 11/2006 | Pinchasik et al. |
| 7,329,277 B2 | 2/2008 | Addonizio et al. |
| 7,520,892 B1 | 4/2009 | Ainsworth et al. |
| 7,625,398 B2 | 12/2009 | Clifford et al. |
| 7,686,843 B2 * | 3/2010 | Moore ............ 623/1.16 |
| 2001/0017339 A1 | 8/2001 | Brotz et al. |
| 2001/0027339 A1 | 10/2001 | Boatman et al. |
| 2001/0049549 A1 | 12/2001 | Boylan et al. |
| 2002/0019660 A1 | 2/2002 | Gianotti et al. |
| 2002/0065549 A1 | 5/2002 | White et al. |
| 2002/0107560 A1 | 8/2002 | Richter |
| 2002/0111669 A1 | 8/2002 | Pazienza et al. |
| 2002/0151964 A1 | 10/2002 | Smith et al. |
| 2002/0169499 A1 | 11/2002 | Zilla et al. |
| 2003/0055487 A1 * | 3/2003 | Calisse ............ 623/1.15 |
| 2003/0083736 A1 | 5/2003 | Brown et al. |
| 2003/0114918 A1 | 6/2003 | Garrison et al. |
| 2003/0120334 A1 | 6/2003 | Gerbeding |
| 2004/0051201 A1 | 3/2004 | Greenhalgh et al. |
| 2004/0093073 A1 | 5/2004 | Lowe et al. |
| 2004/0102836 A1 | 5/2004 | Fischell et al. |
| 2004/0126405 A1 | 7/2004 | Sahatjian et al. |
| 2004/0193250 A1 * | 9/2004 | Von Oepen et al. ......... 623/1.16 |
| 2004/0230293 A1 | 11/2004 | Yip et al. |
| 2004/0236407 A1 | 11/2004 | Fierens et al. |
| 2004/0243220 A1 | 12/2004 | Gianotti et al. |
| 2005/0004650 A1 | 1/2005 | Oepen et al. |
| 2005/0004651 A1 | 1/2005 | Von Oepen et al. |
| 2005/0004658 A1 | 1/2005 | Oepen et al. |
| 2005/0004659 A1 | 1/2005 | Von Oepen et al. |
| 2005/0004662 A1 | 1/2005 | Von Oepen et al. |
| 2005/0043777 A1 | 2/2005 | Von Oepen et al. |
| 2005/0043778 A1 | 2/2005 | Von Oepen et al. |
| 2005/0075716 A1 | 4/2005 | Yan |
| 2005/0222671 A1 | 10/2005 | Schaeffer et al. |
| 2006/0015173 A1 | 1/2006 | Clifford et al. |
| 2006/0106452 A1 | 5/2006 | Niermann |
| 2006/0142844 A1 | 6/2006 | Lowe et al. |
| 2006/0175727 A1 | 8/2006 | Fierens et al. |
| 2006/0184232 A1 | 8/2006 | Gianotti et al. |
| 2006/0206195 A1 | 9/2006 | Calisse |
| 2006/0247759 A1 | 11/2006 | Burpee et al. |
| 2007/0021827 A1 | 1/2007 | Lowe et al. |
| 2007/0021834 A1 | 1/2007 | Young et al. |
| 2007/0135891 A1 | 6/2007 | Schneider |
| 2007/0179593 A1 | 8/2007 | Fierens et al. |
| 2007/0179601 A1 | 8/2007 | Fierens et al. |
| 2007/0213800 A1 | 9/2007 | Fierens et al. |
| 2007/0299505 A1 | 12/2007 | Gregorich et al. |
| 2008/0077231 A1 * | 3/2008 | Heringes et al. ............ 623/1.15 |
| 2008/0294240 A1 | 11/2008 | Casey |
| 2009/0163992 A1 | 6/2009 | Osman et al. |
| 2009/0163996 A1 | 6/2009 | Bregulla |
| 2009/0163997 A1 | 6/2009 | Casey |
| 2009/0163998 A1 | 6/2009 | Casey |
| 2010/0114297 A1 | 5/2010 | Calisse |
| 2011/0004289 A1 | 1/2011 | Von Oepen et al. |
| 2011/0022159 A1 | 1/2011 | Fierens et al. |

FOREIGN PATENT DOCUMENTS

| | | |
|---|---|---|
| DE | 19840645 | 3/2000 |
| EP | 0357003 | 3/1990 |
| EP | 0221570 | 1/1991 |
| EP | 0699451 | 3/1996 |
| EP | 0709067 | 5/1996 |
| EP | 0808614 | 11/1997 |
| EP | 0815806 | 1/1998 |
| EP | 0928605 | 7/1999 |
| EP | 0950386 | 10/1999 |
| EP | 0983753 | 3/2000 |
| EP | 1042997 | 10/2000 |
| EP | 1095631 | 5/2001 |
| EP | 1516600 | 3/2005 |
| FR | 2774279 | 8/1999 |
| GB | 2344053 | 5/2000 |
| JP | 7-24072 | 1/1995 |
| JP | 08-206226 | 8/1996 |
| JP | 09-010318 | 1/1997 |
| JP | 10-328216 | 12/1998 |
| JP | 11-299901 | 2/1999 |
| JP | 2000312721 | 11/2000 |
| WO | WO91/17789 | 11/1991 |
| WO | WO96/21404 | 7/1996 |
| WO | WO96/25124 | 8/1996 |
| WO | WO97/12563 | 4/1997 |
| WO | WO97/12564 | 4/1997 |
| WO | WO97/14375 | 4/1997 |
| WO | WO98/32412 | 7/1998 |
| WO | WO98/47447 | 10/1998 |
| WO | WO99/07308 | 2/1999 |
| WO | WO99/17680 | 4/1999 |
| WO | WO99/23976 | 5/1999 |
| WO | WO99/38456 | 8/1999 |
| WO | WO99/38458 | 8/1999 |
| WO | WO99/39660 | 8/1999 |
| WO | WO99/49928 | 10/1999 |
| WO | WO00/13611 | 3/2000 |
| WO | WO00/32241 | 6/2000 |
| WO | WO00/45744 | 8/2000 |
| WO | WO00/53119 | 9/2000 |
| WO | WO01/01885 | 1/2001 |
| WO | WO01/82835 | 11/2001 |
| WO | WO02/026164 | 4/2002 |
| WO | WO02/064061 | 8/2002 |
| WO | WO02/064065 | 8/2002 |
| WO | WO02/094127 | 11/2002 |
| WO | WO03/009779 | 2/2003 |
| WO | WO03/057076 | 7/2003 |
| WO | WO2004/087015 | 10/2004 |
| WO | WO2006/055533 | 5/2006 |
| WO | WO2006/066886 | 6/2006 |
| WO | WO2006/099449 | 9/2006 |
| WO | WO2008/042618 | 4/2008 |
| WO | WO2008/142566 | 11/2008 |
| WO | WO2009/046973 | 4/2009 |
| WO | WO2009/080326 | 7/2009 |
| WO | WO2009/080327 | 7/2009 |

OTHER PUBLICATIONS

U.S. Appl. No. 60/637,495, filed Dec. 20, 2004, Fierens et al.
U.S. Appl. No. 09/582,318, mailed Aug. 14, 2002, Office Action.
U.S. Appl. No. 09/582,318, mailed Mar. 7, 2003, Notice of Allowance.
U.S. Appl. No. 09/742,144, mailed Sep. 24, 2002, Office Action.
U.S. Appl. 09/742,144, mailed May 14, 2003, Office Action.
U.S. Appl. No. 09/742,144, mailed Aug. 29, 2003, Notice of Allowance.
U.S. Appl. No. 09/916,394, mailed Aug. 12, 2003, Office Action.

U.S. Appl. No. 09/916,394, mailed Oct. 9, 2003, Office Action.
U.S. Appl. No. 09/916,394, mailed Mar. 2, 2004, Office Action.
U.S. Appl. No. 09/967,789, mailed Sep. 17, 2003, Office Action.
U.S. Appl. No. 09/967,789, mailed Feb. 17, 2004, Notice of Allowance.
U.S. Appl. No. 10/241,523, mailed Aug. 18, 2004, Office Action.
U.S. Appl. No. 10/241,523, mailed Oct. 25, 2004, Office Action.
U.S. Appl. No. 10/241,523, mailed Mar. 8, 2005, Office Action.
U.S. Appl. No. 10/241,523, mailed Jun. 3, 2005, Office Action.
U.S. Appl. No. 10/241,523, mailed Aug. 23, 2005, Office Action.
U.S. Appl. No. 10/241,523, mailed Nov. 16, 2005, Office Action.
U.S. Appl. No. 10/241,523, mailed Apr. 27, 2006, Office Action.
U.S. Appl. No. 10/743,857, mailed Mar. 15, 2007, Office Action.
U.S. Appl. No. 10/743,857, mailed Nov. 16, 2007, Office Action.
U.S. Appl. No. 10/743,857, mailed May 8, 2008, Office Action.
U.S. Appl. No. 10/743,857, mailed Jan. 6, 2009, Office Action.
U.S. Appl. No. 10/743,857, mailed May 27, 2009, Office Action.
U.S. Appl. No. 10/743,857, mailed Feb. 12, 2010, Notice of Allowance.
U.S. Appl. No. 10/743,857, mailed Jun. 25, 2010, Notice of Allowance.
U.S. Appl. No. 10/859,636, mailed Jun. 1, 2007, Office Action.
U.S. Appl. No. 10/859,636, mailed Dec. 31, 2007, Office Action.
U.S. Appl. No. 10/859,636, mailed Apr. 15, 2008, Office Action.
U.S. Appl. No. 10/859,636, mailed Oct. 1, 2008, Notice of Allowance.
U.S. Appl. No. 10/859,636, mailed Mar. 5, 2009, Office Action.
U.S. Appl. No. 10/859,636, mailed Oct. 19, 2009, Notice of Allowance.
U.S. Appl. No. 10/859,636, mailed Feb. 1, 2010, Notice of Allowance.
U.S. Appl. No. 10/859,636, mailed May 19, 2010, Notice of Allowance.
U.S. Appl. No. 10/884,613, mailed Mar. 30, 2005, Office Action.
U.S. Appl. No. 10/884,613, mailed Nov. 14, 2005, Office Action.
U.S. Appl. No. 10/903,013, mailed Mar. 15, 2007, Office Action.
U.S. Appl. No. 10/903,013, mailed Nov. 19, 2007, Office Action.
U.S. Appl. No. 10/903,013, mailed May 14, 2008, Office Action.
U.S. Appl. No. 10/903,013, mailed Jan. 5, 2009, Office Action.
U.S. Appl. No. 10/903,013, mailed May 27, 2009, Office Action.
U.S. Appl. No. 10/903,013, mailed Feb. 12, 2010, Notice of Allowance.
U.S. Appl. No. 10/903,013, mailed Jun. 24, 2010, Notice of Allowance.
U.S. Appl. No. 10/903,014, mailed Mar. 15, 2007, Office Action.
U.S. Appl. No. 10/903,014, mailed Nov. 16, 2007, Office Action.
U.S. Appl. No. 10/903,014, mailed May 13, 2008, Office Action.
U.S. Appl. No. 10/903,014, mailed Jan. 13, 2009, Office Action.
U.S. Appl. No. 10/903,014, mailed Jun. 1, 2009, Office Action.
U.S. Appl. No. 10/903,014, mailed Feb. 5, 2010, Notice of Allowance.
U.S. Appl. No. 10/903,014, mailed May 26, 2010, Office Action.
U.S. Appl. No. 10/903,014, mailed Jun. 24, 2010, Notice of Allowance.
U.S. Appl. No. 10/903,080, mailed Mar. 15, 2007, Office Action.
U.S. Appl. No. 10/903,080, mailed Nov. 19, 2007, Office Action.
U.S. Appl. No. 10/903,080, mailed May 12, 2008, Office Action.
U.S. Appl. No. 10/903,080, mailed Dec. 30, 2008, Office Action.
U.S. Appl. No. 10/903,080, mailed May 27, 2009, Office Action.
U.S. Appl. No. 10/903,080, mailed Jan. 13, 2010, Notice of Allowance.
U.S. Appl. No. 10/909,117, mailed Aug. 22, 2007, Office Action.
U.S. Appl. No. 10/909,117, mailed May 12, 2008, Office Action.
U.S. Appl. No. 10/909,117, mailed Dec. 30, 2008, Office Action.
U.S. Appl. No. 10/909,117, mailed May 27, 2009, Office Action.
U.S. Appl. No. 10/909,117, mailed Jan. 13, 2010, Notice of Allowance.
U.S. Appl. No. 10/909,118, mailed Mar. 29, 2007, Office Action.
U.S. Appl. No. 10/909,118, mailed Nov. 19, 2007, Office Action.
U.S. Appl. No. 10/909,118, mailed May 12, 2008, Office Action.
U.S. Appl. No. 10/909,118, mailed Jan. 5, 2009, Office Action.
U.S. Appl. No. 10/909,118, mailed Jul. 24, 2009, Office Action.
U.S. Appl. No. 10/909,118, mailed Jan. 13, 2010, Notice of Allowance.
U.S. Appl. No. 10/954,948, mailed Mar. 15, 2007, Office Action.
U.S. Appl. No. 10/954,948, mailed Nov. 16, 2007, Office Action.
U.S. Appl. No. 10/954,948, mailed May 15, 2008, Office Action.
U.S. Appl. No. 10/954,948, mailed Jan. 13, 2009, Office Action.
U.S. Appl. No. 10/954,948, mailed May 29, 2009, Office Action.
U.S. Appl. No. 10/954,948, mailed Jan. 13, 2010, Notice of Allowance.
U.S. Appl. No. 10/954,948, mailed Jul. 6, 2010, Notice of Allowance.
U.S. Appl. No. 10/955,425, mailed Mar. 15, 2007, Office Action.
U.S. Appl. No. 10/955,425, mailed Nov. 16, 2007, Office Action.
U.S. Appl. No. 10/955,425, mailed May 13, 2008, Office Action.
U.S. Appl. No. 10/955,425, mailed Jan. 13, 2009, Office Action.
U.S. Appl. No. 10/955,425, mailed May 28, 2009, Office Action.
U.S. Appl. No. 10/955,425, mailed Feb. 26, 2010, Notice of Allowance.
U.S. Appl. No. 10/955,425, mailed Jun. 25, 2010, Notice of Allowance.
U.S. Appl. No. 11/313,110, mailed Jan. 8, 2008, Office Action.
U.S. Appl. No. 11/313,110, mailed Jul. 2, 2008, Office Action.
U.S. Appl. No. 11/313,110, mailed Mar. 3, 2009, Office Action.
U.S. Appl. No. 11/313,110, mailed Nov. 2, 2009, Notice of Allowance.
U.S. Appl. No. 11/313,110, mailed Feb. 18, 2010, Notice of Allowance.
U.S. Appl. No. 11/313,110, mailed Jun. 15, 2010, Notice of Allowance.
U.S. Appl. No. 11/404,450, mailed Feb. 4, 2009, Office Action.
U.S. Appl. No. 11/404,450, mailed Mar. 17, 2009, Office Action.
U.S. Appl. No. 11/404,450, mailed Sep. 30, 2009, Office Action.
U.S. Appl. No. 11/404,450, mailed Apr. 22, 2010, Office Action.
U.S. Appl. No. 11/435,260, mailed Jan. 10, 2008, Office Action.
U.S. Appl. No. 11/435,260, mailed Mar. 26, 2008, Office Action.
U.S. Appl. No. 11/435,260, mailed Dec. 16, 2008, Office Action.
U.S. Appl. No. 11/435,260, mailed Jun. 18, 2009, Notice of Allowance.
U.S. Appl. No. 11/435,260, mailed Jun. 26, 2009, Notice of Allowance.
U.S. Appl. No. 11/601,475, mailed Jul. 22, 2008, Office Action.
U.S. Appl. No. 11/601,475, mailed Jan. 6, 2009, Office Action.
U.S. Appl. No. 11/601,475, mailed Jun. 1, 2009, Office Action.
U.S. Appl. No. 11/601,475, mailed Jan. 15, 2010, Notice of Allowance.
U.S. Appl. No. 11/601,475, mailed Jul. 9, 2010, Notice of Allowance.
U.S. Appl. No. 11/731,820, mailed Jan. 27, 2010, Office Action.
U.S. Appl. No. 11/731,820, mailed Aug. 5, 2010, Notice of Allowance.
U.S. Appl. No. 11/731,882, mailed Feb. 3, 2010, Office Action.
U.S. Appl. No. 11/732,244, mailed Sep. 28, 2009, Office Action.
U.S. Appl. No. 11/732,244, mailed May 5, 2010, Notice of Allowance.
U.S. Appl. No. 11/732,244, mailed Jun. 21, 2010, Notice of Allowance.
U.S. Appl. No. 11/961,290, mailed May 6, 2009, Office Action.
U.S. Appl. No. 11/961,290, mailed Dec. 18, 2009, Office Action.
U.S. Appl. No. 11/961,384, mailed May 26, 2009, Office Action.
U.S. Appl. No. 11/961,384, mailed Oct. 8, 2009, Office Action.
U.S. Appl. No. 11/961,754, mailed Jul. 22, 2009, Office Action.
U.S. Appl. No. 11/961,754, mailed Apr. 5, 2010, Notice of Allowance.
U.S. Appl. No. 11/961,754, mailed Jul. 28, 2010, Notice of Allowance.
U.S. Appl. No. 11/973,707, mailed Mar. 19, 2010, Office Action.
U.S. Appl. No. 11/961,775, mailed Oct. 1, 2009, Office Action.
U.S. Appl. No. 11/961,775, mailed Mar. 31, 2010, Office Action.
U.S. Appl. No. 12/949,481, filed Nov. 18, 2010, Schneider.
U.S. Appl. No. 12/966,916, filed Dec. 13, 2010, Casey.
U.S. Appl. No. 10/743,857, mailed Aug. 18, 2010, Issue Notification.
U.S. Appl. No. 10/859,636, mailed Dec. 9, 2010, Notice of Allowance.
U.S. Appl. No. 10/903,013, mailed Aug. 18, 2010, Issue Notification.
U.S. Appl. No. 10/903,014, mailed Aug. 25, 2010, Issue Notification.

U.S. Appl. No. 10/903,080, mailed Sep. 16, 2010, Notice of Allowance.
U.S. Appl. No. 10/909,117, mailed Sep. 16, 2010, Notice of Allowance.
U.S. Appl. No. 10/909,117, mailed Nov. 17, 2010, Issue Notification.
U.S. Appl. No. 10/909,118, mailed Sep. 21, 2010, Notice of Allowance.
U.S. Appl. No. 10/955,425, mailed Sep. 30, 2010, Issue Notification.
U.S. Appl. No. 11/313,110, mailed Sep. 29, 2010, Issue Notification.
U.S. Appl. No. 11/404,450, mailed Nov. 26, 2010, Office Action.
U.S. Appl. No. 11/731,820, mailed Dec. 16, 2010, Notice of Allowance.
U.S. Appl. No. 11/731,882, mailed Sep. 1, 2010, Office Action.
U.S. Appl. No. 11/732,244, mailed Sep. 22, 2010, Issue Notification.
U.S. Appl. No. 11/961,754, mailed Nov. 23, 2010, Issue Notification.

* cited by examiner

FLEXIBLE STENT WITH ELEVATED SCAFFOLDING PROPERTIES

FIELD OF THE INVENTION

The present invention relates to a medical device. More particularly, the present invention relates to a flexible stent that provides elevated scaffolding properties.

BACKGROUND OF THE INVENTION

Atherosclerosis, sometimes called the hardening or clogging of the arteries, is an accumulation of cholesterol and fatty deposits, called plaque, on the inner walls of the arteries. Atherosclerosis causes a partial or total blockage of the arteries and, consequently, a reduced blood flow to the heart, legs, kidneys, or brain.

Traditionally, clogged arteries has been treated with surgical procedures that involve the removal of the diseased arterial tract. Angioplastic procedures, during which a stent is inserted in the diseased portion of the artery, have gained increased acceptance during the last two decades because of the reduced complexity of the procedure, with a consequent reduction in risk and discomfort to the patient.

Figure 1:
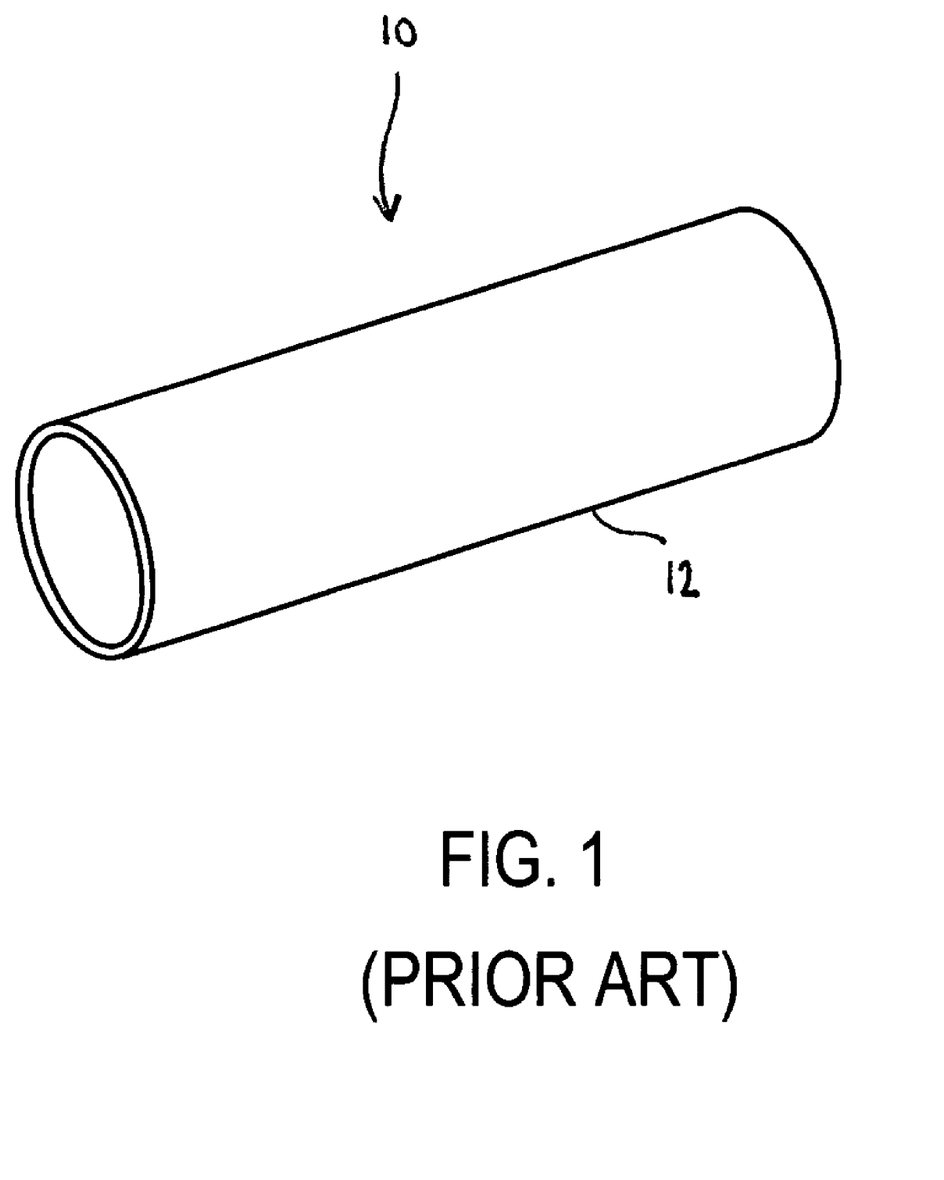
FIG. 1 is a perspective view of an essentially tubular body of a stent.

Referring first to FIG. 1, a stent 10 is a small tubular element that typically has a cylindrical structure 12 and that, once placed within a blocked vessel, acts as a scaffold to keep the vessel open. Stent 10 may be implanted in a bodily vessel by disposing the stent over a balloon tipped catheter and by subsequently inflating the balloon at a target location. Alternatively, stent 10 may be caused to self-expand without the use of a balloon by manufacturing stent 10 from a shape memory material and disposing stent 10 over a catheter in a contracted delivery configuration, successively allowing stent 10 to self-expand at the target location.

One type of self-expanding stent is produced from a superelastic material and is compressed inside a sheath into the contracted delivery configuration. When the stent is released from the sheath, the flexible material causes the stent to spring back to its original shape and size before compression. Another type of self-expanding stent is produced from a thermo-elastic shape-memory material that is formed into a desired size and shape and is then annealed at a temperature higher than a transition temperature. After cooling the stent to a temperature below the transition temperature, the stent becomes soft and can be reduced to a smaller size by compression, so that it can be delivered to the target location, where the stent is warmed to a temperature above the transition temperature, returning to the preprogrammed size and shape.

The following description relates to a balloon expandable stent, but it will be appreciated that a self-expanding stent may be employed instead of the balloon expandable stent, when a clinician believes that self-expansion provides more desirable properties than balloon expansion, for example, due to stent recoil problems.

Figures 2A, 2B:
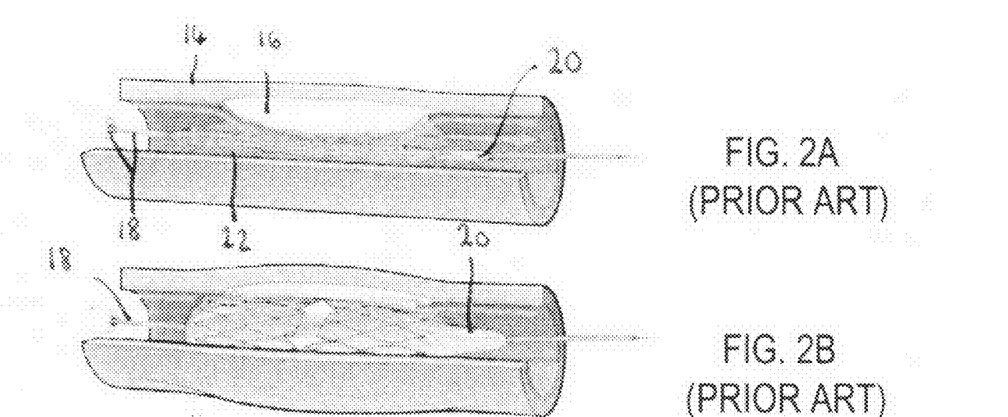
FIGS. 2A-2C are illustrations of a procedure for implanting a stent in a bodily vessel.
Figure 2C:
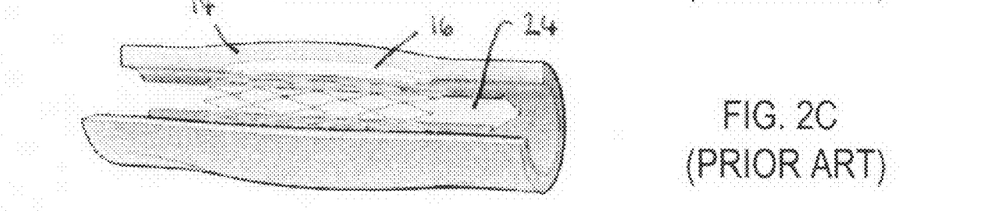

With reference to FIGS. 2A-2C, the placement of a stent 22 into an artery 14 having a buildup of plaque 16 is performed with a very thin tube called catheter 18. The distal end of catheter 18 contains a deflated balloon 20, onto which stent 22 is disposed in a contracted delivery configuration. Balloon tipped catheter 18 is inserted, using local anesthesia, into artery 14 with a needle puncture, typically in the groin, and is guided through the vascular system until its tip reaches the blocked tract of the artery. Balloon 20 is then inflated, deploying stent 22 until contact with the walls of artery 14 is achieved. The deployment of stent 22 causes plaque 16 to become compressed against the walls of artery 14 and also causes artery 14 to be widened and supported, improving blood flow 24.

Figure 3A:
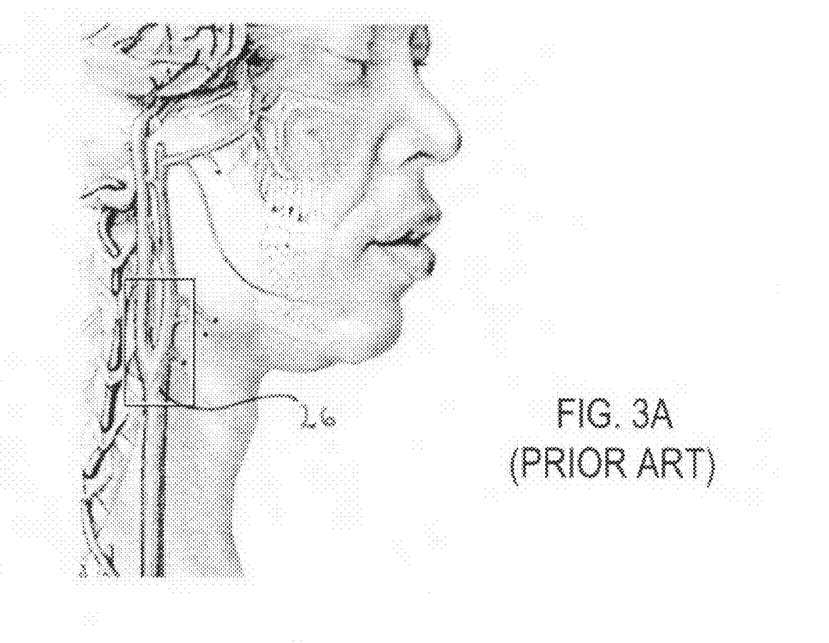
FIGS. 3A-3C are respectively illustrations of the anatomy of the carotid artery, of plaque buildup in a carotid artery, and of a carotid endarterectomy procedure.
Figure 3B:
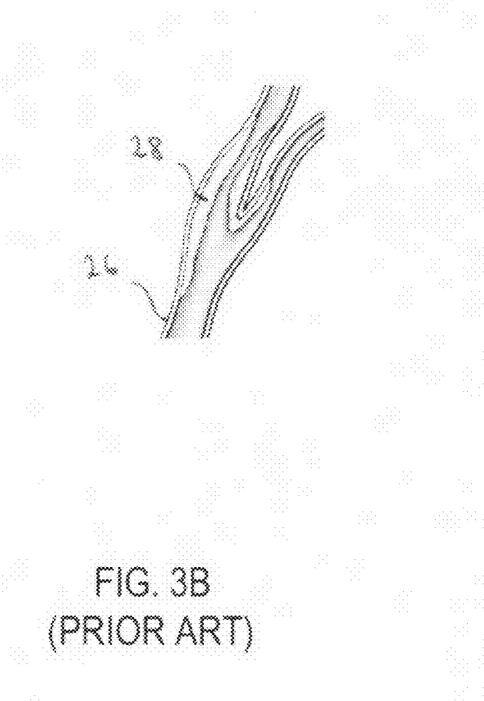
Figure 3C:
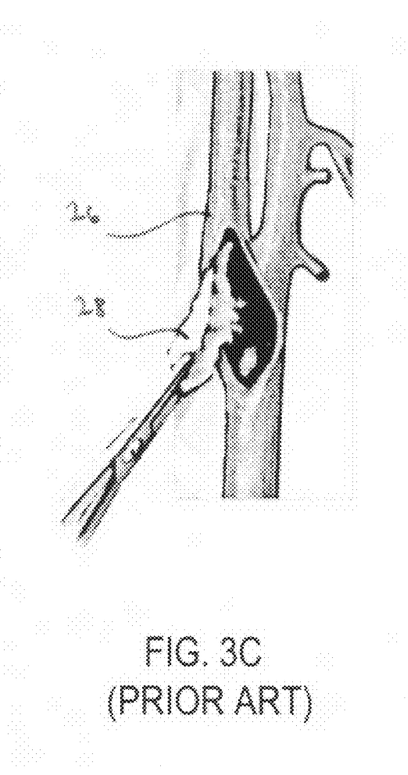

Carotid arteries may experience a significant amount of plaque build-up. The nature of the plaque varies considerably, but in a significant number of cases plaque may not only narrow the carotid arteries, but pieces of the plaque may break away and cause neurological impairment by blocking blood flow to specific areas of the brain. With reference to FIGS. 3A-3C, stenting of carotid artery 26 is complicated by the bifurcated disposition of carotid artery 26. As shown more particularly in FIG. 3A, carotid artery 26 travels from the heart to the head through the neck, supplying vital oxygen and glucose-rich blood to the parts of the brain where thinking, personality, speech, and sensory and motor functions reside. As shown in greater detail in FIGS. 3B-3C, plaque on carotid arteries 26 can be removed through a surgical procedure called carotid endarterectomy, which involves cutting an incision in the neck of the patient and in artery 26 at the site of the carotid artery blockage. Artery 26 is isolated, and plaque 28 and diseased portions of artery 26 are surgically removed. Artery 26 is then sewn back together, improving blood flow to the brain and lessening the probability of a stroke.

An alternative procedure for treating blockage of the carotid arteries is carotid angioplasty, during which a carotid artery stent is inserted inside carotid artery 26 at the site of blockage, providing a scaffolding of carotid artery 26 that keeps carotid artery 26 open and that reduces the risk of plaque becoming loose and reaching brain vessels. During carotid angioplasty, only local anesthesia is used as a tiny incision is made in the groin, and the patient remains alert and awake during the procedure, reducing recovery time.

The bifurcated anatomy and frequent movements of carotid artery 26 require that stents with a high degree of flexibility be employed for carotid angioplasty. Carotid stents in the prior art are formed as a metal mesh or, in general, as a web structure that provides some degree of flexibility. Each of the stent designs in the prior art, however, increases flexibility by increasing cells size in the mesh or web structure. Therefore, whenever stent flexibility is increased in stent in the prior art, scaffolding support is affected negatively.

An example of prior art stent is disclosed in U.S. Pat. No. 5,104,404 to Wolff, which teaches an articulated stent in which stent segments, formed by diamond-shaped cells disposed in ring form, are connected one to the other at some but not all of the tips of the diamond-shaped cells. This arrangement provides for a stent with a high degree of longitudinal flexibility, but also for limited support to the arterial walls at the junctions areas between the different stent segments.

U.S. Pat. No. 5,449,373 to Pinchasik also discloses a stent formed by a plurality of longitudinal stent segments that are connected one to the other by arched segments. This arrangement enables only a limited degree of longitudinal translation between the stent segments, reducing stent flexibility, and also causes one stent segment to rotate in relation to the neighboring segment when tensile or compressive forces are applied to the stent.

U.S. Pat. No. 6,190,403 to Fischell discloses a stent having a plurality of stent segments that are disposed in longitudinal order. Each of the stent segments is formed by longitudinally-oriented cells disposed circumferentially and is joined to a neighboring stent segment by sinusoidal connectors connecting cell tips that are longitudinally aligned one with the other. The stent of the '403 patent provides an elevated degree of scaffolding to the arterial walls, but its structure allows only a limited degree of longitudinal flexibility, due to the limited extent of longitudinal translation between the stent segments that is possible when a compressive force is applied, because this translation is limited to the distance between adjacent stent segments.

U.S. Pat. No. 7,029,493 to Majercak et al. discloses a stent structure having a plurality of wavy rings, joined one to the other by connecting neighboring crests of adjacent rings with curvilinear connectors. Because the ring crests are longitudinally aligned, the degree of motion of the different rings under compressive stress is necessarily limited to the distance between neighboring crests.

Therefore, it would be desirable to provide a stent that generates an elevated degree of scaffolding to a bodily vessel while remaining highly flexible.

It would also be desirable to provide a stent, in which adjacent stent segments can translate one with respect to the other for a distance greater than the distance existing between neighboring rings when the stent is at rest.

BRIEF SUMMARY OF THE INVENTION

A stent according to the present invention generates an elevated degree of support to a bodily vessel while retaining a highly flexible structure.

In one embodiment, a stent constructed according to the principles of the present invention includes an essentially tubular body formed by a closed cell web structure that is configured to expand from a contracted delivery configuration to an expanded deployed configuration and that includes a plurality of longitudinally adjacent web rings. Each of the web rings, or crowns, is composed of a plurality of web elements disposed circumferentially around the longitudinal axis of the stent and adjoined sequentially one to the other with junction bends. Each junction bend in a first web ring is coupled to another junction bend in a neighboring web ring by a S-shaped connector, but the coupled junction bends are not longitudinally aligned one to the other but instead are laterally offset.

Each of the crowns in a web ring is formed by a central member of essentially linear shape that is joined to terminal end members extending from the central element at an obtuse angle. The crowns of each web ring are nested one into the other in the contracted delivery configuration of the stent. Preferably, the crowns of one web ring are oriented at 180 degrees (that is, have an inverted orientation) with respect to the crowns of a neighboring ring.

The S-shaped connector is formed by two arms that are joined by a curvilinear segment. Upon application of a bending force on the stent, for example, when the stent is disposed along a tortuous path or when the patient moves, the two arms translate one in relation to the other by deforming the curvilinear segment, thereby providing flexibility to the stent. Because the junction bends coupled by the S-shaped connector are laterally offset, the junction bends are enabled to translate in response to a compressive force, but do not abut one against the other, but instead translate one sideways in relation to the other, increasing the length of translation of the junction bends and the degree of flexibility of the stent.

With this configuration, the S-shaped connector effectively deforms to suit the movement of the crowns and provides greater flexibility to closed cell stent designs than stent designs in the prior art. The flexibility of the stent may be further tailored to specific applications by providing S-shaped connectors with the same the cross sectional areas as the crowns, or by providing S-shaped connectors and crowns with different cross-sectional areas.

Methods of use of the stent according to the present invention are also provided.

BRIEF DESCRIPTION OF THE SEVERAL VIEWS OF THE DRAWINGS

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF EMBODIMENTS OF THE INVENTION

The present invention relates to stent designs that provide an elevated degree of scaffolding to a bodily vessel while retaining a highly flexible structure. A preferred application of the present invention relates to closed cell stents, in particular, carotid stents, for which lesion scaffolding and the capability of conforming to tortuous anatomies are key design features.

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 4:
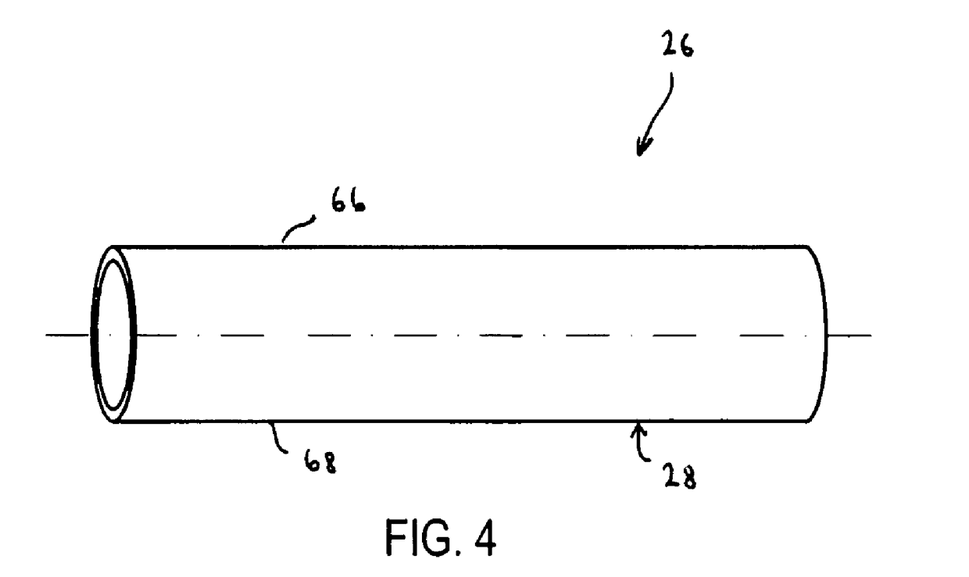
FIG. 4 is a schematic view of the tubular body of one embodiment of a stent according to the present invention.

Referring to FIG. 4, a stent 26 constructed according to the principles of the present invention includes an essentially tubular body 28 expandable from a contracted delivery configuration to an expanded deployed configuration. While body 28 is depicted in FIG. 4 as cylindrical in shape, body 28 may be provided with other shapes, for example, with a frustoconical shape or with the shape of a hyperboloid.

Figure 5:
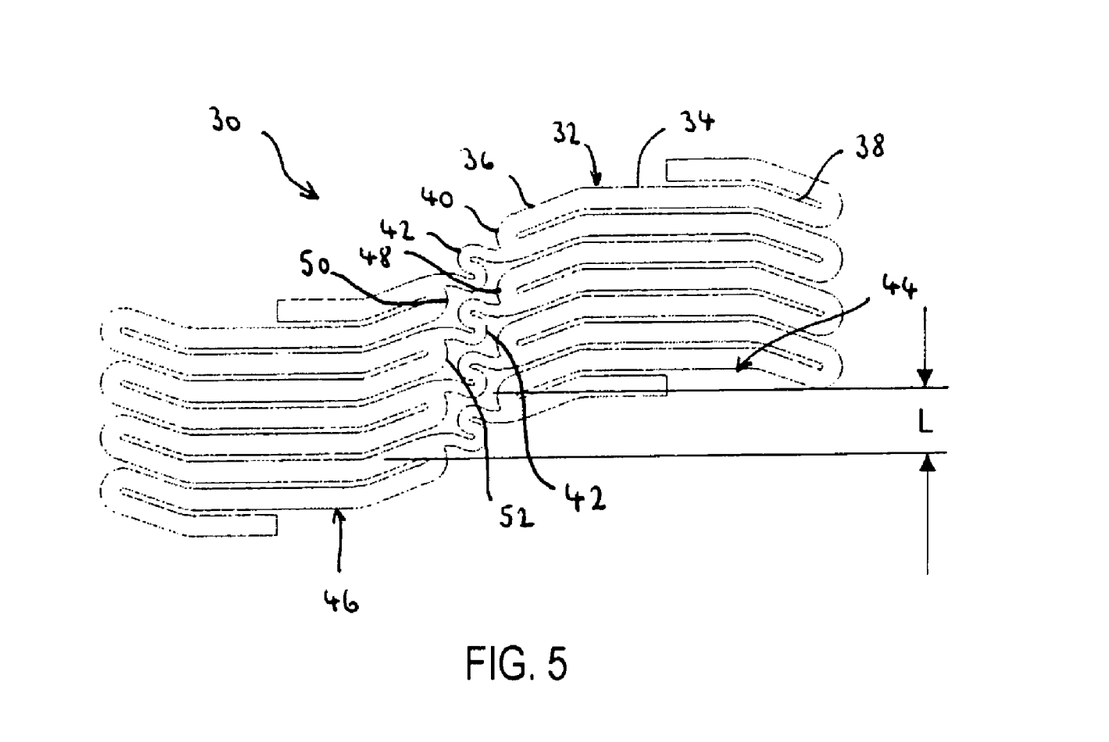
FIG. 5 is a detail plan view of the web structure of a stent according to one embodiment of the present invention.

Referring now to FIG. 5, body 28 is defined by a web structure 30, which includes a plurality of web elements, shaped as crowns 32 in the illustrated embodiment. In particular, each crown 32 includes a central member 34 having a first end member 36 and a second end member 38 extending respectively from the ends of central member 34. Central member 34, first end member 36 and second end member 38 are each essentially linear in shape, and, in the contracted delivery configuration of stent 26, central member 34 is disposed essentially perpendicular to the longitudinal axis of body 28, while first and second members 36 and 38 extend from central member 34 at obtuse angles. Preferably, first and second members 36 and 38 extend from central member 34 at the same angle, but in other embodiments, first and second members 36 and 38 may extend from central member 34 at different angles. In still other embodiments, one or more of central member 34 and first and second members 36 and 38 may be non-rectilinear and have a curved shape.

Crowns 32 are nested one into the other in the contracted delivery configuration and are sequentially adjoined at one end by a junction bend 40 having an essentially arcuate shape. Crowns 32 are disposed circumferentially about the longitudinal axis of body 28 to form web rings 44 and 46, which are joined one to the other by S-shaped connectors 42. As shown in FIG. 5, the crowns in one web ring may be disposed with an orientation that is opposite to the orientation of the crowns in a neighboring web ring. In particular, the crowns in web ring 44 are disposed with an orientation that is 180 degrees different from the orientation of the crowns in web ring 46.

Crowns 32 and S-shaped connectors 42 are typically manufactured from a biocompatible material, and, in one embodiment, may be made of a biodegradable material when it is expected that only temporary vessel support is required. In another embodiment, only S-shaped connectors 42 may be manufactured from a biodegradable material, so that the scaffolding provided by stent 26 may change over time and S-shaped connectors 42 will gradually dissolve in the fluid carried by the vessel (for example, blood), leaving web rings 44 and 46 intact and allowing web rings 44 and 46 to be disposed at specific angles as required by the patient's anatomy or by the movements of the patient's body.

As also shown in FIG. 5, S-shaped connectors 42 do not adjoin two longitudinally aligned junction bends of neighboring web rings, for example, junction bends 48 and 50 from web rings 44 and 46. S-shaped connectors 42 adjoin instead two junction bends from neighboring web rings that are offset one in relation to the other, such as junction bends 48 and 52. This offset configuration is more advantageous than a configuration linking adjacent S-shaped connectors, because the configuration with S-shaped connectors 42 linking offset junction bends 48 and 52 provides greater flexibility to stent 26 than a configuration with S-shaped connectors 42 linking adjacent junction bends 48 and 50, as described in greater detail below. At the same time, vessel patency is maintained in the expanded deployed configuration by the elevated degree of scaffolding caused by disposing S-shaped connectors 42 to extend from each junction of a web ring, rather than from selected junctions only. Therefore, stent 26 is well suited for delivery and implantation both at sites that require elevated flexibility and elevated scaffolding, for example, in carotid arteries.

S-shaped connectors 42 may join adjacent junction bends 48 and 52 at different points within the junction bends. For example, in the embodiment shown in FIG. 5, S-shaped connector 42 adjoins the nearest points of junction bends 48 and 52 by extending from the lowest points of junction bend 48 to the highest point of junction bend 52, providing for an improved nesting of S-shaped connectors 42 within the structure of stent 26. Its should be understood that in other embodiments S-shaped connectors may join junction bends 48 and 52 at different points of the junction bends.

FIG. 5 further shows that each of the junction bend is connected to an adjacent junction bend, causing stent 26 to be configured as a closed cell stent, different from open cell stents, in which only one every predetermined number of junction bends (for example, one every three) is connected to another junction bend. This design increase stent density and due to the relatively small cell sizes.

The mode of operation of stent 10 is illustrated further in FIGS. 4, 6, 7 and 8A-8C. Turning first to FIG. 4, its is known that, when body 28 of stent 26 is in a stationary, at rest condition, upper surface 66 and lower surface 68 of body 28 are subject neither to compressive or tensile forces. When elongated body 28 is bent, in the manner illustrated in FIG. 6, upper surface 66 becomes subject to a longitudinal compressive force C, while lower surface 68 becomes subject to a longitudinal tensile force T.

Figure 6:
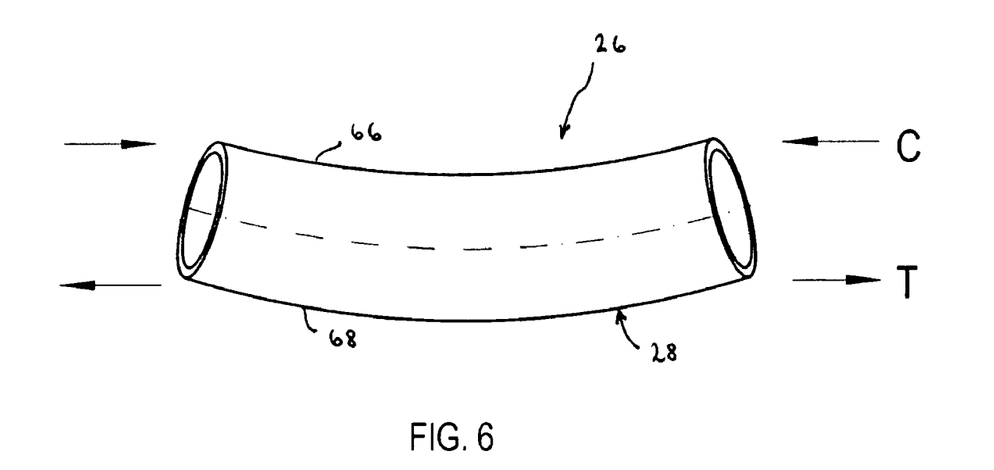
FIG. 6 is an illustrative example of a tubular body in a flexed position.

If body 28 is formed by open cells, the cells of compressed surface 66 will decrease in size, while the cells of tensed surface 68 will expand. Such expansion of the cell openings is problematic in a carotid stents, because of the related reduction in arterial scaffolding.

Figure 7:
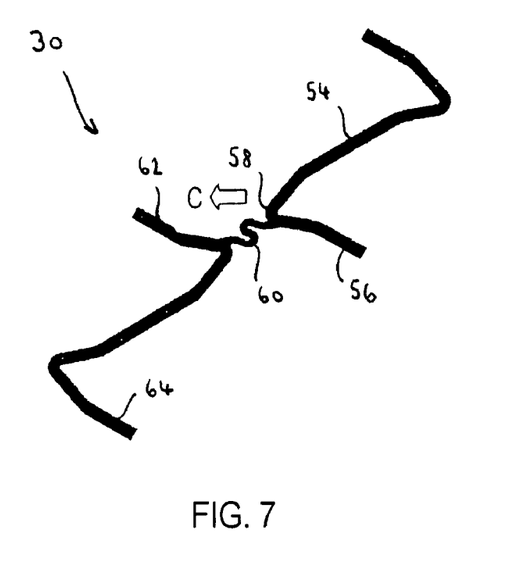
FIG. 7 is a schematic plan view of a S-shaped connector connecting two neighboring junction bends in one embodiment of the present invention.

Turning now to FIG. 7, crowns 54 and 56 become spread apart one in relation to the other during the expansion of stent 26 while remaining adjoined by junction bend 58. At the same time, the presence of S-shaped connector 60 causes crowns 54, 56 not to become longitudinally displaced from crowns 62, 64. Therefore, S-shaped connectors 60 cause stent 26 to maintain a substantially homogeneous scaffolding during expansion and prevents some cells from expanding to a greater extent than others, as may occur with open cell stents.

Figure 8A:
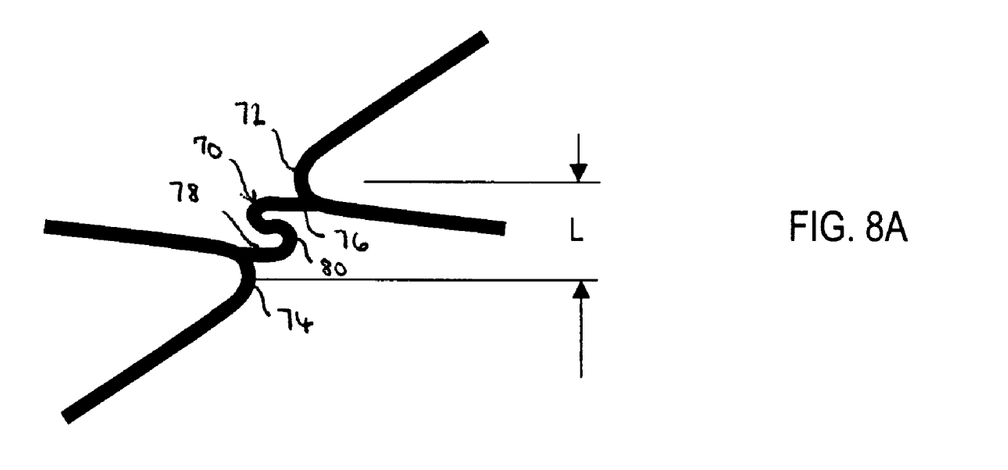
FIGS. 8A-8C are schematic plan views of a S-shaped connector in one embodiment of the present invention when at rest and in compressed and tensed positions.
Figure 8B:
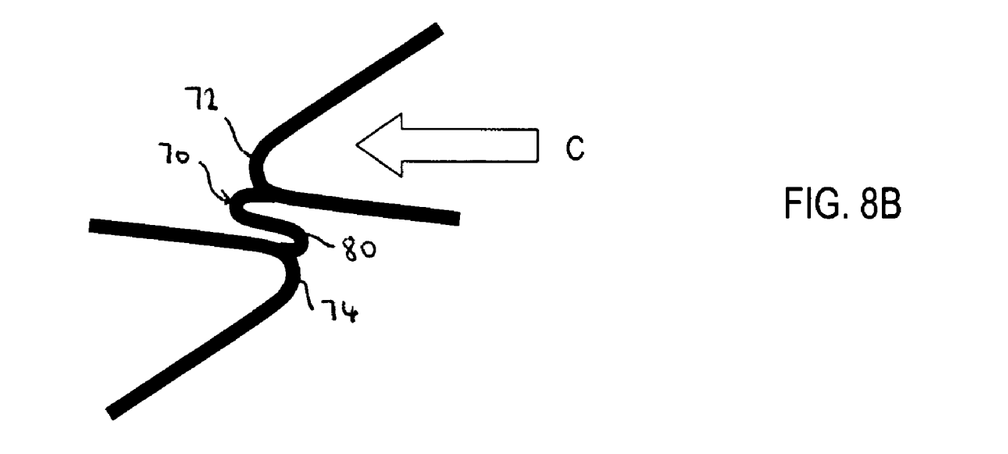
Figure 8C:
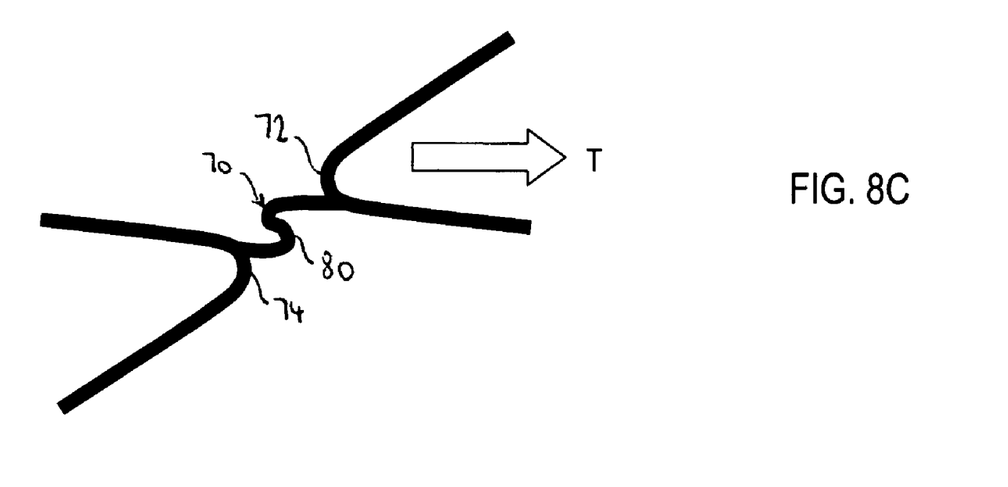

Turning now to FIGS. 8A-8C, the disposition of S-shaped connectors 70 also provides elevated flexibility to stent 26 while still maintaining the desired degree of scaffolding. In particular, FIG. 8A illustrates the at-rest configuration of an embodiment a S-shaped connector, identified by reference numeral 70, which connects junction bends 72 and 74 by extending from the lower end of junction bend 72 to the upper end of junction bend 74. The S-shape of connector 70 is composed of two essentially parallel arms 76 and 78 that are joined by a curvilinear segment 80. In other embodiments, S-shaped connector 70 may extends from different points of junction bends 76 and 78, and the S-shape may have a plurality of other configurations, for example, with curvilinear arms. The junction bends coupled by S-shaped connector 70 are offset by a distance L, allowing junction bends 72 and 74 to move laterally one in relation to the other, and, accordingly, allows the crowns connected to those junction bends also to move laterally one in relation to the other.

Turning now to FIG. 8B, upon application of a compressive force C, junction bends 72 and 74 and the crowns connected thereto become closer one to the other because curvilinear segment 80 deforms inwards, allowing the arms of S-shaped connector 70 to slide one in relation to the other. Therefore, junction bend 72 may translate past junction bend 74, to become situated proximally of junction bend 74, thereby increasing the ability of stent 26 to flex in comparison to stents in the prior art.

With further reference to FIG. 8C, when a tensile force T is applied, S-shaped connector 70 stretches by deforming curvilinear segment 80 outwards, thereby allowing junction bends 72 and 74 to move laterally one away from the other, so that stent 26 can bend to a significant degree. At the same time, junction bends 72 and 74 remain connected one to the other, thereby limiting the relative separation of junction bend 72 from junction bend 74 and retaining the scaffolding support of the walls of the vessel, within which stent 26 is implanted. Flexibility of the stent may be further tailored to desired results by varying the cross-sectional areas of the S-shaped connector 54 in relation to the neighboring crowns.

Stent 26 may include different features known in the art to provide certain beneficial properties. For example but not by way of limitation, stent 26 may be coated with a therapeutic coating that includes a bioactive agent, or may contain radio-opaque markers, or may be coupled to a fabric that prevents the passage of emboli from the vessel wall into the blood stream.

Stent 26 may be disposed into a target vessel location, such a location within a carotid artery, by inserting a guide wire into the artery, and by successively translating a catheter along the guide wire that carries the stent in a contracted condition. When the stent has reached the target location, as may be determined by tracking radio-opaque markers embedded in the stent, a balloon disposed on the catheter and within the stent is inflated, causing the stent to expand from the contracted condition to the deployed condition until contact with the vessel walls is achieved. Alternatively, if the stent is manufactured from a self-expanding material, after the target location has been reached, a sheath covering the stent is withdrawn, enabling the stent to self-expand until contact with the vessel walls is made and a support structure is created.

By providing a stent having a structure formed by web elements disposed in web rings and connected by S-shaped elements in the manner described herein, so to form a closed cell structure, an improved support is provided to the vessel walls in comparison with open cell stents, and a highly flexible structure is achieved that provides scaffolding support to the vessel walls even when the vessel is bent.

It should be notes that, while the invention has been described in connection with the above described embodiments, it is not intended to limit the scope of the invention to the particular forms set forth, but on the contrary, it is intended to cover such alternatives, modifications, and equivalents as may be included within the scope of the invention. Accordingly, the scope of the present invention fully encompasses other embodiments that may become obvious to those skilled in the art and the scope of the present invention is limited only by the appended claims.

What is claimed is:

1. A stent comprising:
   a web structure defining an essentially tubular body expandable from a contracted delivery configuration to an expanded deployed configuration;
   a plurality of longitudinally adjacent web rings defining the web structure, each web ring including a plurality of sequentially adjoined web elements disposed substantially parallel to a longitudinal axis of the essentially tubular body when in the contracted delivery configuration, pairs of the plurality of sequentially adjoined web elements being sequentially adjoined at junction bends,
   wherein each junction bend in a first web ring of the plurality of longitudinally adjacent web rings is connected to a second junction bend in a neighboring web ring of the plurality of longitudinally adjacent web rings by a S-shaped connector having a plurality of segments disposed one in relation to the other in step-wise configuration, a central segment of the plurality of segments within the connector is disposed in a direction essentially parallel to the longitudinal axis of the essentially tubular body: and
   two junction bends of the junction bends connected by the S-shaped connector being laterally offset one in relation to the other with the central segment of the connector being disposed within a gap disposed between the two junction bends and radially offset from both of the two junction bends.

2. The stent of claim 1, wherein each of the web elements comprises a central member having a first and a second ends, wherein the central member is disposed essentially parallel to the longitudinal axis in the contracted delivery configuration, wherein the central member is connected at the first end to a first end member at a first obtuse angle, and wherein the central member is connected at the second end to a second end member at a second obtuse angle.

3. The stent of claim 2, wherein the first and the second obtuse angles are essentially equal.

4. The stent of claim 2, wherein the web elements of each web ring are nested one into the other in the contracted delivery configuration, and wherein the junction bends have an arcuate shape.

5. The stent of claim 2, wherein the web elements in the first web ring are oriented at approximately 180 degrees in relation to the web elements in the neighboring web ring.

6. The stent of claim 1, wherein the two essentially parallel segments translate one in relation to the other upon application of a bending force on the essentially tubular body, thereby providing flexibility to the essentially tubular body.

7. The stent of claim 1, wherein the S-shaped connectors have a cross-sectional area different from the cross-sectional area of the web elements.

8. The stent of claim 1, wherein the web structure is manufactured from a biocompatible material.

9. The stent of claim 1, wherein at least the S-shaped connectors are manufactured from a biodegradable material.

10. The stent of claim 1, wherein the web structure is configured to self-expand from the contracted delivery configuration to the expanded deployed configuration.

11. The stent of claim 10, wherein the web structure is manufactured from a shape memory material.

12. The stent of claim 1, wherein the web structure is configured to expand from the contracted delivery configuration to the expanded deployed configuration by application of pressure to an interior surface of the essentially tubular body.

13. The stent of claim 1, wherein pressure is applied to the interior surface by expanding an inflatable balloon disposed within the essentially tubular body.

14. The stent of claim 1, further comprising a coating disposed on the web structure, the coating comprising a bioactive agent.

15. A method of stenting a bodily vessel comprising:
   providing a stent having a web structure defining an essentially tubular body expandable from a contracted delivery configuration to an expanded deployed configuration, a plurality of longitudinally adjacent web rings defining the web structure, each web ring including a plurality of sequentially adjoined web elements, the web elements being disposed substantially parallel to a longitudinal axis of the essentially tubular body in the contracted delivery configuration, pairs of the plurality of sequentially adjoined web elements being sequentially adjoined at a junction bend, each junction bend in a first web ring of the plurality of longitudinally adjacent web rings being connected to a second junction bend in a neighboring web ring of the plurality of longitudinally adjacent web rings by a S-shaped connector to define the web structure, the S-shaped connector comprises a plurality of segments disposed one in relation to the other in step-wise configuration, a central segment of the plurality of segments within the connector being disposed in a direction essentially parallel to the longitudinal axis of the essentially tubular body, two junction bends connected by the S-shaped connector being laterally offset one in relation to the other with the central segment of the connector being disposed within a gap disposed between the two junction bends and radially offset from both of the two junction bends;

disposing the stent in the contracted delivery configuration in the bodily vessel; and causing the stent to expand from the contracted delivery configuration to the expanded deployed configuration, thereby providing a supporting structure to the bodily vessel.

16. The method of claim 15, wherein the two essentially parallel segments translate one in relation to the other by application of a bending force on the essentially tubular body, thereby providing flexibility to the essentially tubular body.

17. The method of claim 15, further comprising the step of deploying the stent by applying pressure to an interior surface of the essentially tubular body.

18. The method of claim 15, wherein providing the stent comprises providing the web structure configured to self-expand from the contracted delivery configuration to the expanded deployed configuration.

19. A stent comprising:
a web structure defining an essentially tubular body expandable from a contracted delivery configuration to an expanded deployed configuration;
a plurality of longitudinally adjacent web rings defining the web structure, each web ring including a plurality of sequentially adjoined web elements disposed substantially parallel to a longitudinal axis of the essentially tubular body when in the contracted delivery configuration, pairs of the plurality of sequentially adjoined web elements being sequentially adjoined at junction bends, wherein each junction bend in a first web ring of the plurality of longitudinally adjacent web rings is connected to a second junction bend in a neighboring web ring of the plurality of longitudinally adjacent web rings by an S-shaped connector having a plurality of segments disposed one in relation to the other in step-wise configuration, a central segment of the S-shaped connector being disposed in a direction essentially parallel to the longitudinal axis of the essentially tubular body, each S-shaped connected being orientated in the same orientation along the length of the web structure; and
two junction bends of the junction bends connected by the connector being laterally and radially offset one in relation to the other, the central segment of the connector being disposed within a gap formed by the lateral and radial offset of the two junction bends and being radially offset from both of the two junction bends.

20. The stent of claim 19, wherein the web elements of each web ring are nested one into the other in the contracted delivery configuration, and wherein the junction bends have an arcuate shape.

21. The stent of claim 19, wherein the two essentially parallel segments translate one in relation to the other upon application of a bending force on the essentially tubular body, thereby providing flexibility to the essentially tubular body.

22. The stent of claim 19, wherein the web structure is configured to self-expand from the contracted delivery configuration to the expanded deployed configuration.

23. The stent of claim 19, wherein the web structure is configured to expand from the contracted delivery configuration to the expanded deployed configuration by application of pressure to an interior surface of the essentially tubular body.

\* \* \* \* \*